US008210683B2

(12) United States Patent
Geggel

(10) Patent No.: US 8,210,683 B2
(45) Date of Patent: Jul. 3, 2012

(54) NO-HISTORY METHOD FOR INTRAOCULAR LENS POWER ADJUSTMENT AFTER EXCIMER LASER REFRACTIVE SURGERY

(75) Inventor: Harry S. Geggel, Seattle, WA (US)

(73) Assignee: Virginia Mason Medical Center, Seattle, WA (US)

( * ) Notice: Subject to any disclaimer, the term of this patent is extended or adjusted under 35 U.S.C. 154(b) by 176 days.

(21) Appl. No.: 12/843,237

(22) Filed: Jul. 26, 2010

(65) Prior Publication Data

US 2011/0051083 A1 Mar. 3, 2011

Related U.S. Application Data

(60) Provisional application No. 61/237,416, filed on Aug. 27, 2009.

(51) Int. Cl.
*A61B 3/00* (2006.01)
*A61B 3/10* (2006.01)

(52) U.S. Cl. ........................................ 351/246; 351/205

(58) Field of Classification Search .................. 351/205, 351/246

See application file for complete search history.

(56) References Cited

U.S. PATENT DOCUMENTS 5,092,880 A 3/1992 Ohmi
5,282,852 A 2/1994 Capetan et al.
6,626,538 B1 9/2003 Arrowsmith
2002/0105617 A1 8/2002 Norrby et al.
2002/0122153 A1 9/2002 Piers et al.
2003/0053025 A1 3/2003 Turner et al.
2005/0018137 A1 1/2005 Behrendt
2005/0177313 A1 8/2005 Latkany
2006/0028619 A1 2/2006 Fujieda et al.
2007/0093891 A1 4/2007 Tabernero et al.
2008/0231809 A1 9/2008 Haigis
2008/0297724 A1 12/2008 Shimizu et al.
2009/0135372 A1 5/2009 Sarver
2009/0251664 A1 10/2009 Norrby et al.
2009/0281552 A1 11/2009 Hiramatsu et al.
2010/0030225 A1 2/2010 Ianchulev

FOREIGN PATENT DOCUMENTS

RU 2343884 C1 1/2009
WO 20081125198 A1 10/2008
WO 20081148517 A 12/2008

OTHER PUBLICATIONS

Geggel, H.S., Pachymetric Ratio No-History Method for Intraocular Lens Power Adjustment After Excimer Laser Refractive Surgery, American Academy of Ophthalmology, vol. 116, No. 6 (Jun. 2009).

(Continued)

*Primary Examiner* — Jack Dinh

(74) *Attorney, Agent, or Firm* — Davis Wright Tremaine LLP

(57) ABSTRACT

Systems and methods for using a new corneal ratio, referred to as the Geggel ratio, to estimate how much treatment a patient received at an original myopic or mixed astigmatism excimer laser refractive surgery. The Geggel ratio represents the ratio of the measure of a pre-IOL central pachymetry to a measure of a pre-IOL superior pachymetry. The estimated laser ablation depth (ELAD) is used in a derived linear regression equation to determine an IOL power adjustment that is added to the standard SRK/T formula used to determine IOL power.

20 Claims, 4 Drawing Sheets

100

START

MEASURE PHYSICAL CHARACTERISTICS OF AN EYE — 104

DETERMINE AN INITIAL IOL POWER VALUE USING THE MEASURED PHYSICAL CHARACTERISTICS — 108

DETERMINE AN ESTIMATED LASER ABLATION DEPTH (ELAD) USING THE GEGGEL RATIO AND THE MEASURED PHYSICAL CHARACTERISTICS — 112

DETERMINE AN ESTIMATED LASER TREATMENT — 116

DETERMINE AN IOL POWER ADJUSTMENT VALUE USING A DERIVED LINEAR REGRESSION EQUATION — 120

ADD THE IOL POWER ADJUSTMENT VALUE TO THE INITIAL IOL POWER VALUE TO OBTAIN A CORRECTED IOL POWER VALUE — 124

DETERMINE A SELECTABLE IOL POWER VALUE BASED ON THE CORRECTED IOL POWER VALUE — 128

END

OTHER PUBLICATIONS

Shammas, H.J. et al., No-History Method of Intraocular Lens Power Calculation for Cataract Surgery After Myopic Laser in Situ Keratomileusis, Journal of Cataract & Refractive Surgery, vol. 33, Issue 1, pp. 31-36 (Jan. 2007), Abstract only.

Jin, H. et al., Intraocular Lens Power Calculation After Laser Refractive Surgery: Corrective Algorithm for Corneal Power Estimation, Journal of Cataract & Refractive Surgery, vol. 3, Issue 1, pp. 97-96 (Jan. 2010), Abstract only.

Borasio, E. et al., Estimation of True Corneal Power After Keratorefractive Surgery in Eyes Requiring Cataract Surgery: Besst Formula, Journal of Cataract & Refractive Surgery, vol. 32, Issue 12, pp. 2004-2014 (Dec. 2006), Abstract only.

Khalif, M. et al., Prospective Evaluation of Intraocular Lens Calculation After Myopic Refractive Surgery, Journal of Cataract & Refractive Surgery, vol. 24, Issue 1, pp. 33-38 (Jan. 2008), Abstract only.

Diehl, J.W. et al., Intraocular Lens Power Adjustment Nomogram After Laser in Situ Keratomileusis, Journal of Cataract & Refractive Surgery, vol. 35, Issue 9, pp. 1587-1590 (Sep. 2009), Abstract only.

Feiz, V. et al., Nomogram-Based Intraocular Lens Power Adjustment After Myopic Photorefractive Keratectomy and Lasik: A New Approach, Ophthalmology, vol. 112, Issue 8, pp. 1381-1387, (Aug. 2005), Abstract Only.

Masket, S.A. et al., Simple Regression Formula for Intraocular Lens Power Adjustment in Eyes Requiring Cataract Surgery After Excimer Laser Photoablation, Journal of Cataract & Refractive Surgery, vol. 32, Issue 3, pp. 430-434 (Mar. 2006), Abstract only.

Haigis, W., Intraocular Lens Calculation After Refractive Surgery for Myopia: Haigis-L Formula, Journal of Cataract & Refractive Surgery, vol. 34, Issue 10, pp. 1658-1663 (Oct. 2008), Abstract only.

Camellin, M. et al., A New Formula for Intraocular Lens Power Calculation After Refractive Corneal Surgery, Journal of Cataract & Refractive Surgery, vol. 22, Issue 2, pp. 187-199 (2006), Abstract only.

Seitz, B. et al., Intraocular Lens Power Calculation in Eyes After Corneal Refractive Surgery, Journal of Cataract & Refractive Surgery, vol. 16, Issue 3, pp. 349-361 (May-Jun. 2000), Abstract only.

Wang, L. et al., Comparison of Intraocular Lens Power Calculation Methods in Eyes That Have Undergone Lasik, Ophthalmology, vol. 111, Issue 10, pp. 1825-1831 (Oct. 2004), Abstract only.

Colliac, J-P, Matrix Formula for Intraocular Lens Power Calculation, Investigative Ophthalmology & Visual Science, vol. 31, No. 2, pp. 374-381 (Feb. 1990).

Feiz, V., Intraocular Lens Power Calculation After Corneal Refractive Surgery, Middle East Afr J Ophthalmol, vol. 17, Issue 1, pp. 63-68 (2010).

Odenthal, M. et al., Clinical and Theoretical Results of Intraocular Lens Power Calculation for Cataract Surgery After Photorefractive Keratectomy for Myopia, Arch Ophthalmol. vol. 120, pp. 431-438 (2002).

Packer, M. et al., Intraocular Lens Power Calculation After Incisional and Thermal Keratorefractive Surgery, Journal of Cataract & Refractive Surgery, vol. 30, pp. 1430-1434 (2004 ASCRS and ESCRS).

Savini, G., et al., Intraocular Lens Power Calculation After Myopic Refractive Surgery, Ophthalmology, vol. 113, pp. 1271-1282 (2006).

Wang, L. et al., Comparison of Intraocular Lens Power Calculation Methods in Eyes That Have Undergone Laser-Assisted In-Situ Keratomileusis, Trans Am Ophthalmol Soc, vol. 102 pp. 189-197 (2004).

NO-HISTORY METHOD FOR INTRAOCULAR LENS POWER ADJUSTMENT AFTER EXCIMER LASER REFRACTIVE SURGERY

CROSS REFERENCE TO RELATED APPLICATIONS

The present application claims the benefit of provisional application 61/237,416 for "NO-HISTORY METHOD FOR INTRAOCULAR LENS POWER ADJUSTMENT AFTER EXCIMER LASER REFRACTIVE SURGERY" filed on Aug. 27, 2009, which is incorporated herein by reference in its entirety.

BACKGROUND

1. Field

The present disclosure relates to systems and methods for estimating the amount of treatment a patient received during a previous myopic or mixed astigmatism excimer laser refractive surgery, and more particularly, to utilizing this estimation to determine an accurate intraocular lens (IOL) power for subsequent phacoemulsification cataract surgery for the patient.

2. Related Art

The following description includes information that may be useful in understanding the present invention. It is not an admission that any of the information provided herein is prior art or relevant to the presently claimed invention, or that any publication specifically or implicitly referenced is prior art.

It is well known that using standard equations to determine the intraocular lens (IOL) power for routine phacoemulsification cataract surgery in patients with high expectations who have had previous myopic excimer laser photorefractive keratectomy (PRK) or LASIK corneal surgery often leads to unwanted postoperative hyperopia.[1-8] This occurs because the actual central keratometric power is overestimated with current manual or topographic keratometers, the standard lens formulas do not take into account the altered anterior/posterior corneal curvature relationship after excimer ablation, and the effective lens position is erroneously assumed to be more anterior for the Hoffer, SRK/T (Sanders, Retzlaff, Kraff), and Holladay formulas, and to a lesser extent for the Haigis formula.[9-16] Numerous theoretic and empiric approaches to solve this clinical dilemma have been proposed.[3,9-11, 14, 16-41] Some of these methods require pre-refractive surgery keratometry, surgical change in spherical equivalent (SE), or excimer laser data that, for most patients, will not be readily available in the future. Therefore, newer formulas or methods that only require information readily obtained at the actual cataract consultation visit are clinically important for this group of patients.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described.

In this disclosure, a pachymetric method using a new corneal ratio (hereinafter "the Geggel ratio") is proposed to estimate how much treatment a patient received at an original myopic or mixed astigmatism excimer laser refractive surgery. This estimated laser ablation depth (ELAD) is then used in a derived linear regression equation to determine an IOL power adjustment that is added to the standard SRK/T formula used to determine IOL power.

In an embodiment, the invention includes the use of the Geggel ratio and associated mathematical calculations, assumptions and rules as set forth below to determine IOL power in former refractive surgery patients, without any need for historical data. Among other things, this may be useful in connection with routine cataract surgery. In various embodiments, the aforementioned Geggel ratio and associated mathematical calculations, assumptions and rules may be embodied in software, may reside on a computer-readable medium, may be implemented via a network, may be incorporated in one or more medical devices, or any combination thereof.

Figure 1:
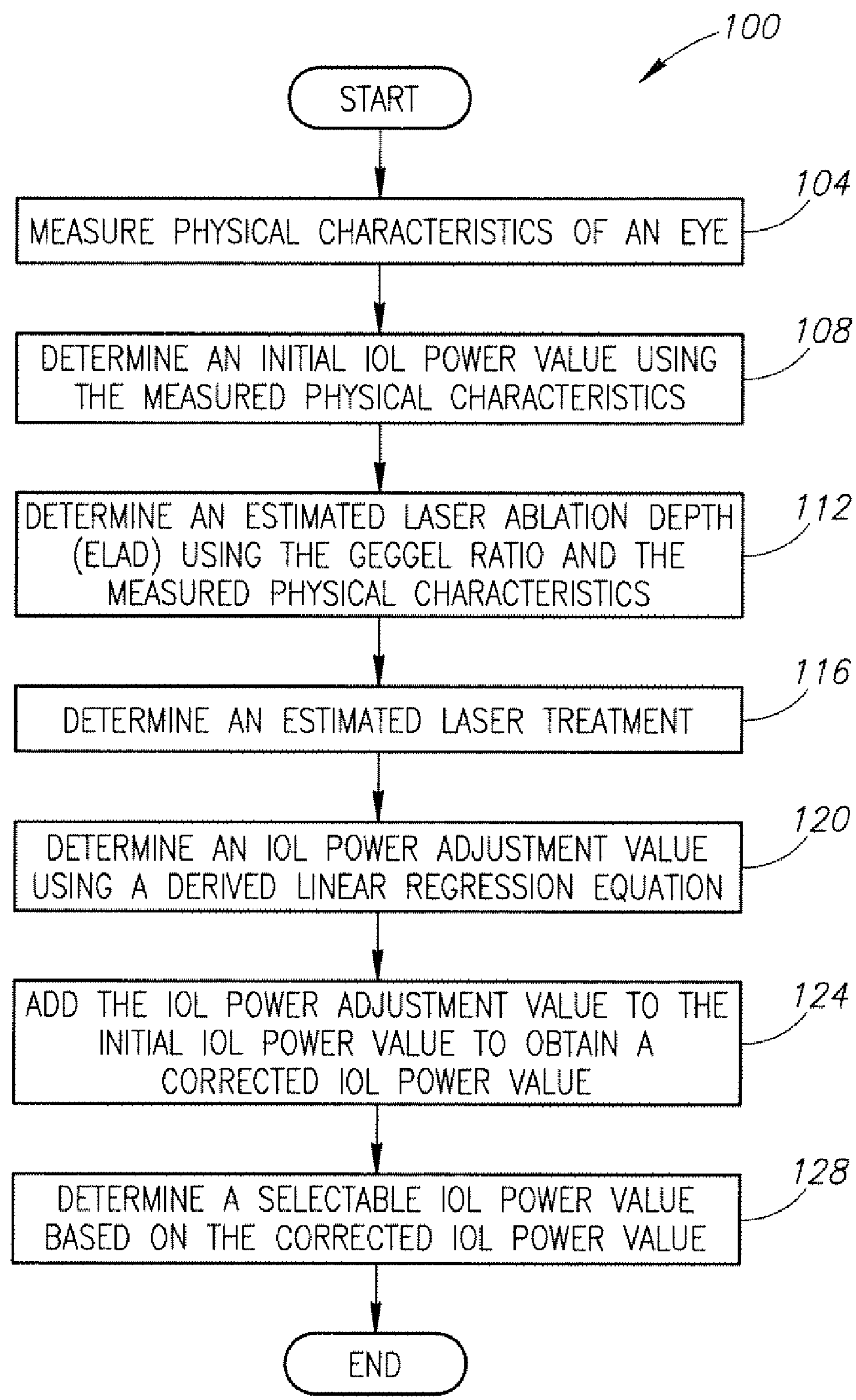
FIG. 1 illustrates a flow diagram for a process for determining an IOL power using a new corneal ratio (referred to herein as "the Geggel ratio") for a patient that has had previous myopic or mixed astigmatism excimer laser refractive surgery.

FIG. 1 illustrates a flow diagram for a process 100 for determining an IOL power value using the Geggel ratio for a patient that has had previous myopic or mixed astigmatism excimer laser refractive surgery. Initially, various physical characteristics of a patient's eye are measured (step 104). Such measurements include corneal topography, corneal pachymetry, manual central keratometry, and axial length measurement.

Figure 3:
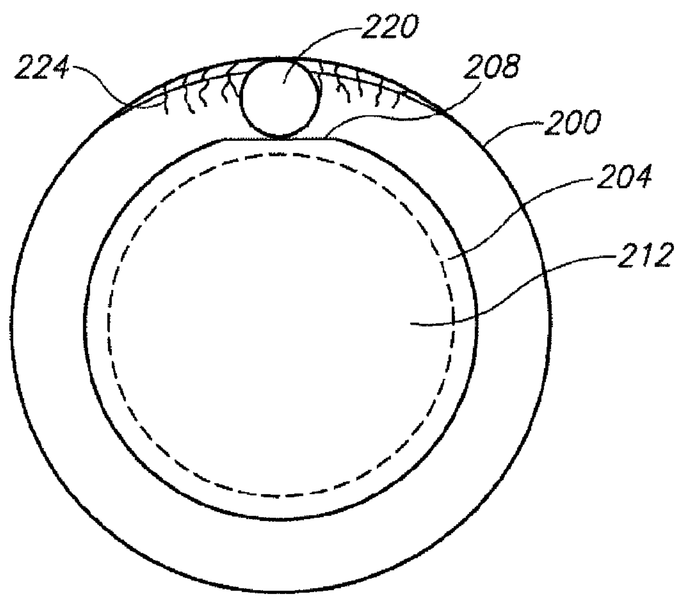
FIG. 3 illustrates a schematic of a cornea of a patient that has had previous myopic or mixed astigmatism excimer laser refractive surgery, and further illustrates the positioning of a pachymeter probe used to measure the superior corneal pachymetry (SCP).

In addition to the aforementioned measurements, the superior corneal pachymetry (SCP) is measured at a slit lamp using a pachymeter. As shown in FIG. 3, to obtain this measurement, an examiner may place the tip of a pachymeter probe 220 orthogonal to the 12 o'clock corneal/limbal junction of a cornea 200 with the patient looking slightly down. FIG. 3 also shows the cornea 200 as having a superior pannus 224, a flap dissection area 204 with a superior hinge, and an excimer laser ablation area 212. The SCP measurement is relatively straightforward in most patients with clear, distinct superior corneal contours. However, in corneas such as the one shown in FIG. 3 with a superior pannus 224, the examiner should follow the visible corneal limbus clockwise from ten o'clock and counterclockwise from two o'clock toward the twelve o'clock location and place the superior edge of the tip of the pachymeter probe 220 where the real limbus actually begins and the inferior edge onto the cornea 200. The average reading from 6 to 10 measurements may be calculated to determine the superior corneal pachymetry measurement.

The central pachymetry (CP) is also measured with the seated patient blinking 2 to 3 times before looking straight ahead with the examiner standing to the side, using his dominant hand to minimize error, and taking 6 to 10 measurements in the central cornea. The thinnest reading may be taken as the central measurement.

Once the central keratometry and axial length measurements have been obtained, an initial IOL power value may be calculated for the eye using the measured characteristics and the SRK/T formula, which is a formula widely used by those skilled in the art to determine IOL power (step 108). As discussed below, this initial IOL power value will be modified to obtain a corrected IOL power value (or "Geggel IOL power").

The process 100 further includes determining an estimated laser ablation depth (ELAD) using the Geggel ratio and the CP and SCP measurements (step 112). This determination is more specifically described below with reference to FIG. 2.

The use of the Geggel ratio is based on the assumption that the ratio of the central to peripheral corneal pachymetry should stay constant for a given patient. Therefore, without knowing any pre-excimer laser surgery information, one can estimate the actual excimer laser ablation depth and convert this to an estimated number of diopters of treatment at the corneal plane.

Geggel ratios were determined by dividing the pre-IOL central pachymetry (CP) by the pre-IOL superior corneal pachymetry (SCP) in a control group of 207 patients who underwent LASIK/PRK surgery. The Geggel ratios were arbitrarily divided into three groups: a first group having an SCP less than 700 μm, a second group having an SCP between 700 μm and 749 μm, and a third group having an SCP greater than or equal to 750 μm. The resulting Geggel ratios are shown below in Table 1.

TABLE 1

| Geggel Ratios | | | | |
|---|---|---|---|---|
| SCP (μm) | n | Range | Mean ± SD | Mean + 1 SD |
| <700 | 49 | 0.683-0.837 | 0.767 ± 0.036 | 0.803 |
| 701-749 | 96 | 0.650-0.807 | 0.739 ± 0.034 | 0.773 |
| ≧750 | 62 | 0.642-0.798 | 0.725 ± 0.033 | 0.758 |

SCP = superior corneal pachymetry; SD = standard deviation

Using the Geggel ratios from Table 1, and given that the ratio of the central to peripheral corneal pachymetry should stay constant for a particular patient, an estimated laser ablation depth may be calculated using the following equations, wherein CP is the measured central pachymetry, SCP is the measured superior corneal pachymetry, and A is the estimated laser ablation depth (ELAD):

$$(\mathrm{CP}+A)/\mathrm{SCP}=\text{Geggel ratio} \quad \text{Equation (1):}$$

$$A=(\text{Geggel ratio})(\mathrm{SCP})-\mathrm{CP} \quad \text{Equation (2):}$$

To obtain an estimate of the number of diopters of treatment during the previous excimer laser surgery, the amount of tissue removed per diopter of correction for differing versions of VISX software (Advanced Medical Optics, Inc., Santa Ana, Calif.) was calculated for the control group. The results of these calculations are shown below in Table 2.

TABLE 2

| Micrometers of Tissue Ablated per Diopter of Treatment with Differing Versions of VISX Software (Advanced Medical Optics, Inc., Santa Ana, CA) | | |
|---|---|---|
| VISX Version | n | Average Micrometers Removed Per Diopter Treatment |
| 1.51 | 124 | 11.67 |
| 2.5x | 102 | 10.49 |
| 3.xx | 498 | 12.14 |
| 4.xx | 588 | 13.07 |
| 5.xx | 181 | 14.34 |
| Wavescan | 230 | 14.82 |

Using the data shown in Table 2, the estimated laser ablation depth may be converted to obtain an estimate of the number of diopters of treatment at the corneal plane (step 116). This conversion is done by dividing the estimated laser ablation depth by 12, which is near the lowest value of micrometers ablated per diopter of treatment using the VISX software, as can be seen in Table 2. Using this value functions to maximize the estimated diopters treated and minimize the risk of postoperative hyperopia.

Figure 4:
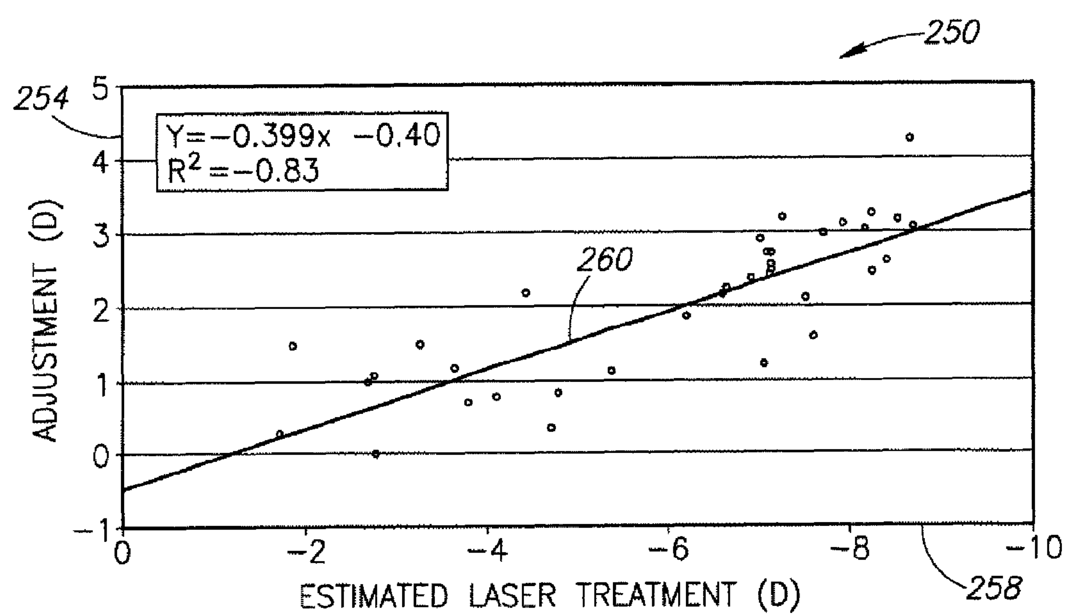
FIG. 4 illustrates a graphical representation of an adjustment to the SRK/T formula as a function of estimated laser treatment in diopters (D) calculated by the pachymetric method.

The process 100 further includes determining an IOL power adjustment value using a derived linear regression equation (step 120). As shown in FIG. 4, the regression equation, $y=-0.399X-0.40$, was calculated from a graph 250 of estimated laser treatment 258 calculated by the pachymetric method versus adjustment 254 to the SRK/T formula, as was performed in Masket and Masket's[14] study. The graph 250 also shows a linear regression line 260 for the regression equation. The adjustment 254 to the IOL power may be determined by subtracting the SRK/T value, calculated using pre-IOL keratometry and axial length, from the ideal IOL power. As can be appreciated, the IOL power adjustment value may be calculated using the regression equation and the estimated laser treatment value determined in step 116.

Once the IOL power adjustment value has been determined, a corrected IOL power value (or "Geggel IOL power") may be obtained by adding the IOL power adjustment value to the previously determined initial IOL power value (step 124).

Additionally, since most commonly used IOLs are only available in 0.5 diopter (D) steps, the corrected IOL power value may not exactly mirror the actual surgeon's choice in selecting an IOL for a given patient.[39] Thus, the process 100 may also include an IOL power calculation (termed "Geggel-real") to determine a selectable IOL power value based on the corrected IOL power value (step 128). For example, to minimize postoperative hyperopia, the following scheme may be used to determine a selectable IOL power, wherein X is an integer number of diopters: for corrected IOL power values of (X−1)+0.4 diopters to (X−1)+0.7 diopters, choose X diopters for the selectable IOL power value, and for corrected IOL power values of (X−1)+0.8 diopters to (X)+0.3 diopters, choose X+0.5 diopters for the selectable IOL power value. As an example, a 20.0 D lens would be selected for calculated Geggel IOL powers in the range of 19.4-19.7 D, and a 20.5 D lens would be selected for calculated Geggel IOL powers in the rage of 19.8 to 20.3 D. As can be appreciated, this scheme may be similarly applied to Geggel IOL powers outside of the range of 19.4 to 20.3 D.

Figure 2:
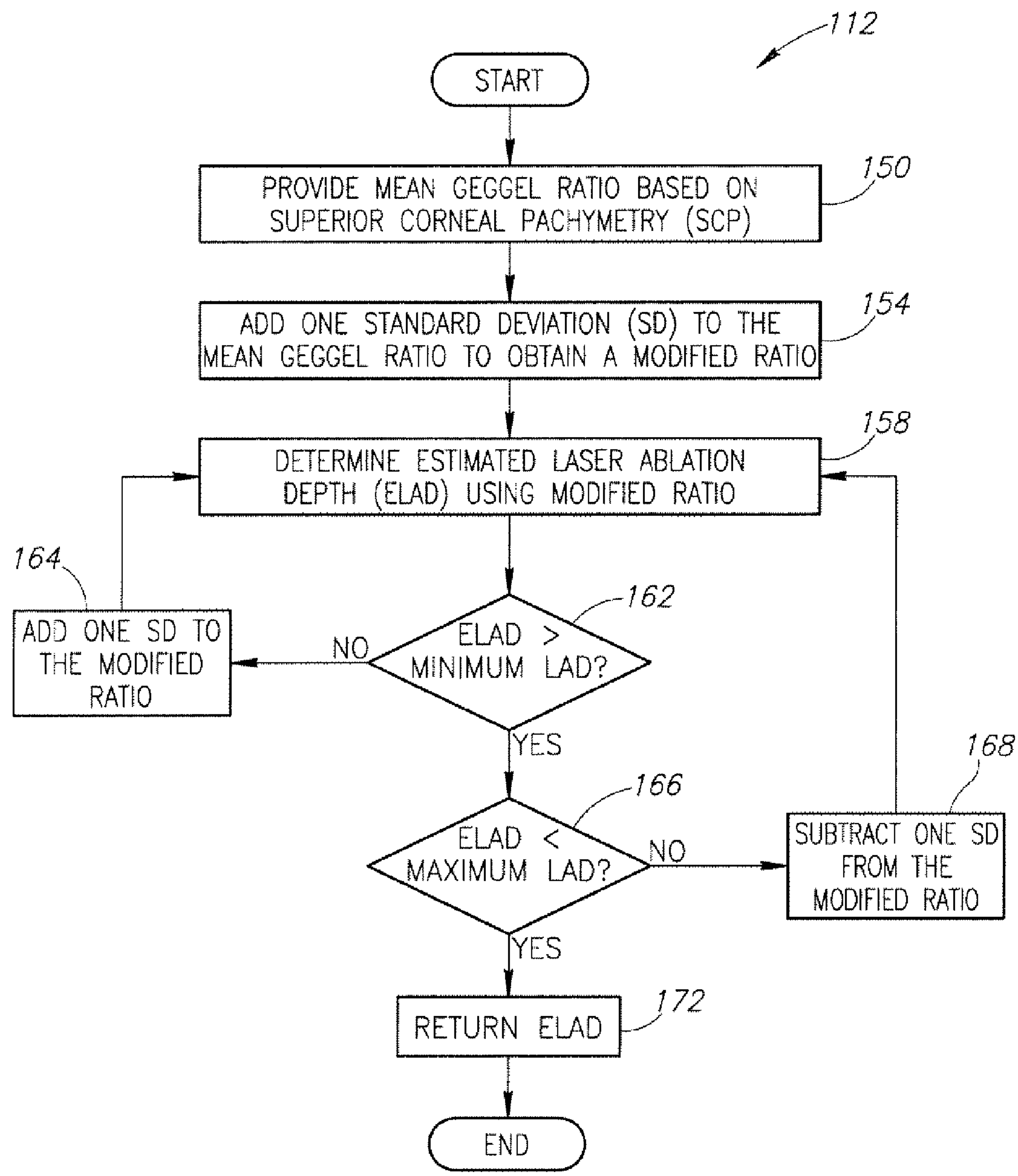
FIG. 2 illustrates a flow diagram for determining an estimated laser ablation depth (ELAD) using the Geggel ratio, wherein the ELAD is used in the process shown in FIG. 1 to determine the IOL power.

FIG. 2 illustrates a flow diagram for determining an estimated laser ablation depth (ELAD) using the Geggel ratios (step 112 shown in FIG. 1), wherein the resulting ELAD is used in the process 100 shown in FIG. 1 to determine an IOL power. Initially, the process includes providing the mean Geggel ratio based on the measured superior corneal pachymetry (step 150). This data may be obtained from Table 1 shown above. For example, the mean Geggel ratio for a measured SCP of 720 μm would be 0.739, since 720 μm is between 701 μm and 749 μm and thus resides in the second group of SCP measurements in Table 1. Similarly, the mean Geggel ratio for a measured SCP of 760 μm would be 0.725, since 760 μm is greater than or equal to 750 μm and thus resides in the third group of SCP measurements.

To minimize the possibility of under correction, one standard deviation (SD) is added to the mean Geggel ratio to obtain a modified ratio (step 154). The resulting estimated laser ablation depth should either be close to the actual number micrometers removed or an overestimation the ablation depth, which will minimize postoperative hyperopia (see FIGS. 5 and 6).

Using the modified ratio and the measured SCP and CP, an estimated laser ablation depth (ELAD) may be calculated (step 158), as described above using Equation (2).

In practice, excimer laser ablations are usually greater than a certain minimum laser ablation depth (LAD), for example, greater than 10 μm. Thus, if the modified ratio returns an ELAD that is less than the minimum LAD (step 162), one SD is added to the modified ratio (step 164) until the resulting ELAD is greater than the minimum LAD (see Case Example 3 below).

Further, excimer laser ablations are generally less than a certain maximum laser ablation depth (LAD). For example, a pachymeter may have an SD of 5 μm, and the actual excimer ablation depth may generally be less than 100 μm, so the maximum LAD may be determined to be 105 μm. Thus, if the ELAD is determined to be greater than the maximum LAD (e.g., greater than 105 μm), one SD may be subtracted from the modified ratio (step 166) until the calculated value for the ELAD is less than the maximum LAD (see case example 4, below). Finally, once an ELAD that satisfies the above-referenced requirements has been obtained, the resulting ELAD may be used in further calculations in the process 100 shown in FIG. 1 (step 172).

Patient Study and Examples

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means without the exercise of inventive capacity and without departing from the scope of the invention.

A retrospective analysis was performed on patients who previously underwent LASIK or PRK who presented with mature cataracts requiring phacoemulsification and posterior chamber IOL implantation at the Virginia Mason Medical Center in Seattle from June 2006 to August 2008. The study was performed with the approval of the Virginia Mason Medical Center Institutional Review Board/Ethics Committee and in accordance with the U.S. Health Insurance Portability and Accountability Act and the Declaration of Helsinki guidelines for human research. The inventor examined 36 eyes of 23 patients (14 male, 9 female, average age 61 years, range 44-75 years, 16 right eyes, 20 left eyes, 31 LASIK, 5 PRK). All patients except one had no concurrent glaucoma, retinal disease, or previous intraocular surgery. One patient had combined cataract/IOL and epiretinal membrane surgery. All patients achieved 20/20 or better best spectacle corrected postoperative visual acuity. The time from the original refractive surgery to cataract surgery averaged 8 years (range, 2-13 years). Twenty-two patients had previous myopic excimer laser treatment (−2.00 to −9.25 diopters [D], average −5.48 D), and 1 patient had mixed astigmatism treatment (manifest refraction: −1.50+2.50X180, SE: −0.25). Four patients (7 eyes) previously had LASIK performed by the inventor, and both the preoperative and operative data were available. Nineteen patients had their refractive surgeries elsewhere, and all attempts were made to retrieve their preoperative and excimer laser data; 14 of these patients had preoperative spectacle or contact lens data verified from old records, and 10 patients had the actual excimer laser printout available. Therefore, actual excimer laser data were available for 14 patients (23 eyes). VISX software was used for 13 of these patients (9 eyes v. 1.51, 5 eyes v. 3.10, 4 eyes v. 3.21, 2 eyes v. 4.51, and 1 eye v. 4.65) and Nidek (Nidek Inc., Fremont, Calif.) software (unknown version) for 1 patient (2 eyes). Thirteen patients had both eyes operated on within a 6-week period. All patients had uncomplicated phacoemulsification surgery with placement of a SN60WF lens (Alcon Laboratories Inc., Fort Worth, Tex.) in the capsular bag; 4 patients (8 eyes) had surgeries performed by 3 of the inventor's partners, and 19 patients had surgery performed by the inventor. The surgical goal was plano in 28 eyes, −0.50 D in 3 eyes, and mono vision (−1.00 to −2.00 D) in 5 eyes. A personalized A-constant of 119.16 was used for all surgeries. No IOL exchanges or piggyback lenses were necessary for any patient.

All eyes had the following preoperative workup: corneal topography (TMS-4, Tomey Corp., Phoenix, Ariz.), corneal pachymetry (DGH pachette 2, DGH Technology, Inc., Exton, Pa.), manual central keratometry (Haag-Streit, Bern, Switzerland), and axial length measurement (optical coherence interferometry with the IOLMaster [Carl Zeiss Meditec AG, Jena, Germany] n=27; immersion A scan [Accutome, Inc., Malvern, Pa.], n=9; mean 25.81±1.37 mm, range 23.57-28.78 mm). In addition, the superior corneal pachymetry and central pachymetry was carefully measured using the methods described herein above.

A separate Excel spreadsheet (Microsoft Corp., Redmond, Wash.) was prepared to tabulate the predicted IOL powers using the following previously published formulas or methods, when applicable, if the necessary pre-LASIK/PRK keratometry or change in SE values was known: Masket, Koch, Ladas, Walter, modified Maloney, clinical history, Feiz (2 methods: standardized approach and nomogram), Latkany average and flat formulas, Ferrara, Rosa, Jin, Seitz, Savini, Shammas (2 methods: no-history equation and regression formula), Awwad, and the new Geggel formula (see below).[9,13-15,18,22-25,27,29,31,33,35,37,41-43] The Koch method used his published tables (double K technique) to calculate the additional power necessary to add to the SRK/T formula.[27] The TMS topography determined the average keratometry used in a modified Maloney equation formula (average keratometry X 1.114−6.1) and Shammas regression formula (average keratometry X 1.14−6.8).[15,33] The Seitz equation subtracted the change in SE multiplied by 0.24 from the average pre-IOL manual keratometry value.[13] The final Awwad results combined the average TMS central 3-mm corneal power (n=27) and SimK no-history data (n=9) using equations 1 and 6, respectively, from the original article.[41] Predicted IOL powers from the modified Maloney, clinical history method (spectacle plane), Shammas (regression formula), Seitz, and Awwad were calculated using optimized SRK/T, Hoffer, and Holladay formulas. The Jin formula used the Holladay 1 formula with a surgical goal of −0.88 D. The Ladas and Walter formulas are identical. SRK/T and Hoffer values were calculated for the former and Holladay 1 values for the latter. The SRK/T formula was used for all other calculations. Because the anterior chamber depth, horizontal corneal diameter, and lens thickness were not available for all patients, the Haigis and Holladay 2 formulas were not evaluated in this study.

Final SEs were determined in all eyes an average of 11.8 (range, 4-30) weeks after cataract surgery. The ideal IOL power was then back calculated according to previously published methods.[21] The expected refractive result was calculated by subtracting the IOL power predicted by each formula from the ideal IOL power and then dividing this number by the value representing the magnitude of IOL power that would produce 1.0 D of refractive change at the spectacle plane (mean 1.35; range 1.20-1.52).[17] Mean±standard deviation (SD), minimum and maximum values, and absolute mean±SD were determined for each formula. The percentage of eyes within the clinically useful postoperative SE range of +0.5 to −1.00 D was calculated along with the number of eyes within ±0.5 D, ±1.0 D, <−1.5 D, and >1.0 D of the surgical goal.[15]

As described above with reference to FIG. 1, the control group of 207 patients who underwent LASIK/PRK also had their central and superior pachymetries measured before refractive surgery and their Geggel ratios (mean±SD, range) calculated using Filemaker software (Apple, Cupertino, Calif.). See Table 1 above. In addition, all patients undergoing refractive surgery (n=1723) were followed with their own Filemaker database and had their preoperative and 3-month central pachymetries measured. The amount of tissue removed per diopter of correction for differing versions of VISX software was calculated (see Table 2).

CASE EXAMPLES

Case 1

A. Preoperative laser manifest Rx: −2.25 (SE −2.25)
B. Axial length 23.99 mm, pre-IOL keratometry: 41.75/43.00; SRK/T value: 21.02 D
C. Laser treatment: 32 μm
 Pre-IOL central pachymetry: 590 μm
 Pre-IOL superior corneal pachymetry: 830 μm
 Mean Geggel ratio+1 SD=0.758
 Geggel ratio technique: (590+A)/830=0.758; A=39.1 μm 39.1 μm/12=−3.26 D
D. −0.399X−3.26−0.40=0.90 D
E. Geggel pachymetry IOL=0.90+21.02=21.92 D
F. IOL proposed: 22.50 D, Ideal IOL: 22.50 D

Case 2

A. Preoperative laser manifest Rx: −7.25−2.00X177 (SE −8.25)
B. Axial length 26.82 mm, pre-IOL keratometry: 37.37/37.75; SRK/T value: 18.09 D
C. Laser treatment: 88 μm
 Pre-IOL central pachymetry: 512 μm
 Pre-IOL superior corneal pachymetry: 822 μm
 Mean Geggel ratio+1 SD=0.758
 Geggel ratio technique: (512+A)/822=0.758; A=111 μm
 Because A>105 μm (maximum LAD), recalculate using the mean value for Geggel ratio (i.e., subtract 1 SD): (512+A)/822=0.725; A=83.95 μm
 83.95 μm/12=−7.00 D
D. −0.399X−7.00−0.40=2.39 D
E. Geggel pachymetry IOL=2.39+18.09=20.48 D
F. IOL proposed: 21.0 D, Ideal IOL: 21.0 D

Case 3

A. Preoperative laser manifest Rx: −0.50−3.00X85 (SE −2.00)
B. Axial length 25.30 mm, pre-IOL keratometry: 42.25/42.00; SRK/T value: 17.94 D (target −0.50 D)
C. Laser treatment: unknown
 Pre-IOL central pachymetry: 606 μm
 Pre-IOL superior corneal pachymetry: 807 μm
 Mean Geggel ratio+1 SD=0.758
 Geggel ratio technique: (606+A)/807=0.758; A=5.7 μm
 Because A<10 μm (minimum LAD), recalculate using 2 SD value for Geggel ratio (i.e., add 1 SD): (606+A)/807=0.791; A=32.34 μm
 32.34 μm/12=−2.69 D
D. −0.399X−2.69−0.40=0.67 D
E. Geggel pachymetry IOL=0.67+17.94=18.61 D
F. IOL proposed: 19.00 D, Ideal IOL: 18.90 D

Case 4

A. Preoperative manifest Rx: unknown
B. Axial length 27.67 mm, pre-IOL keratometry: 36.50/38.25 SRK/T value: 16.21 D
C. Laser treatment: unknown
 Pre-IOL central pachymetry: 377 μm
 Pre-IOL superior corneal pachymetry: 737 μm
 Mean Geggel ratio+1 SD=0.773
 Geggel ratio technique: (377+A)/737=0.773; A=193 μm
 Because A>105 μm (maximum LAD), recalculate using mean value for Geggel ratio (i.e., subtract 1 SD): (377+A)/737=0.739; A=168 μm
 Because A>105 μm, recalculate using 1 SD below mean value for Geggel ratio (i.e., subtract 1 SD): (377+A)1737=0.705; A=143 μm
 Because A>105 μm, recalculate using 2 SD below mean value for Geggel ratio (i.e., subtract 1 SD): (377+A)/737=0.671; A=118 μm
 Because A>105 μm, recalculate using 3 SD below mean value for Geggel ratio (i.e., subtract 1 SD): (377+A)/737=0.637; A=92.47 μm
 92.47 μm/12=−7.71 D
D. −0.399X−7.71−0.40=2.68 D
E. Geggel pachymetry IOL=2.68+16.21=18.89 D
F. IOL proposed: 19.50 D, Ideal IOL: 19.20 D Study Results As noted above, FIG. 4 shows the graph 250 with the derived linear regression formula, y=−0.399X−0.40, for the IOL adjustment 254 added to the SRK/T formula using the estimated amount of laser treatment 258 derived from the Geggel ratio method. A high correlation coefficient (−0.83) was calculated for these 36 eyes.

Figure 5:
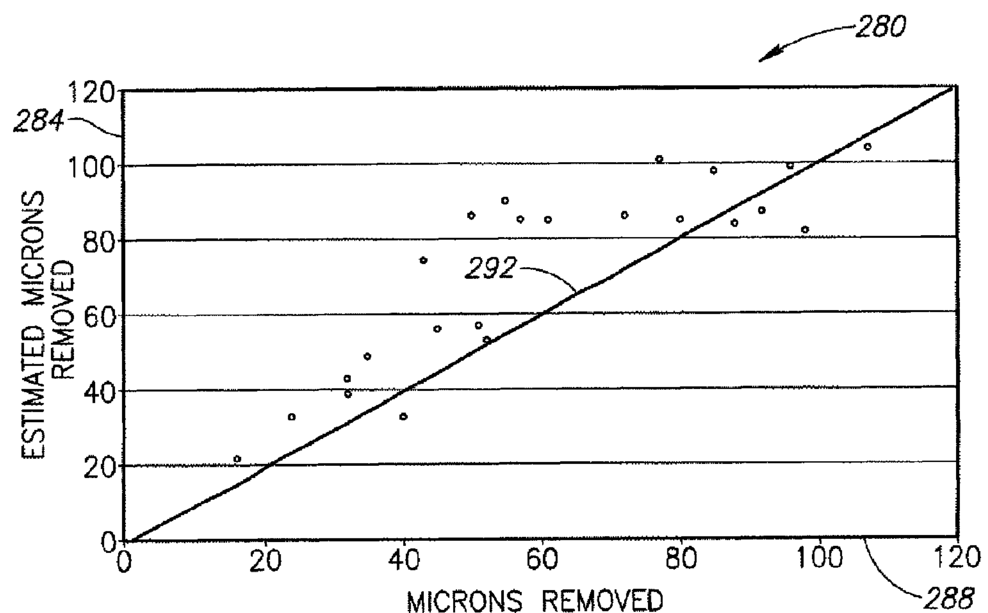
FIG. 5 illustrates a graphical representation of actual laser ablation depth taken from excimer laser reports versus estimated laser ablation depth calculated by the pachymetric method.

FIG. 5 shows a graph 280 which compares the actual micrometers of tissue ablated 288 at surgery for the 23 cases with available operative printouts to the estimated micrometers removed 284 using the Geggel method. A line of identity 292 is also shown. A high correlation coefficient of 0.852 was found. As can be seen, many of the estimated values are higher than the actual values because, as described above, all calculations started with the 1 SD above the mean Geggel ratio to minimize postoperative hyperopia.

Figure 6:
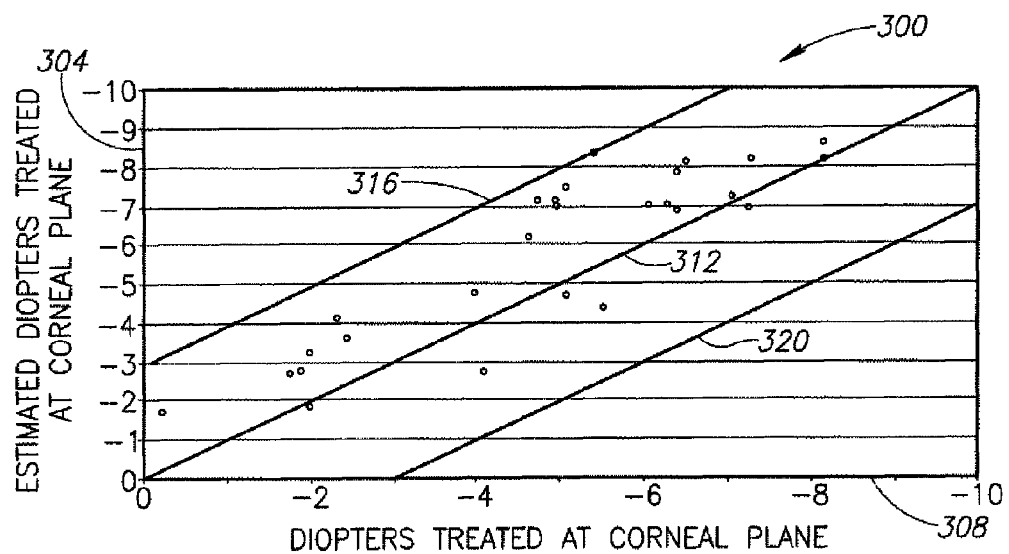
FIG. 6 illustrates a graphical representation of the actual number of diopters (D) treated at the corneal plane versus the estimated number of diopters (D) treated at the corneal plane calculated by the pachymetric method.

FIG. 6 shows a graph 300 that reveals the relationship between diopters treated at the corneal plane 308 for the 27 eyes with available pre-laser and postoperative manifest refractions compared with the estimated treatment values 304 derived from the pachymetric technique. A line of identity 312 as well as a −3 diopter (D) line 320 and a +3 D line 316 are also shown. A high correlation of 0.885 was calculated. As can be seen, the values are easily bracketed by the ±3 D lines 316 and 320, which, according to the Geggel regression formula, represent ±0.8 D.

Tables 3 and 4 below summarize the refractive results for all tested formulas. The Geggel formula had the lowest mean and absolute mean values with no eye having a refraction >1.0 D and 89% between the clinically useful −1.0/+0.5 D range. Using the Geggel-real modification described above pushed the mean value to mild myopia, increased the minimum myopic result, decreased the maximum hyperopic result, and increased the number within the −1.0/+0.5 D range to 92%. Only 4 eyes were hyperopic with the following refractions: 0.23, 0.25, 0.28, and 0.49. Overall, this adjustment is practical from the patient's perspective to minimize hyperopic results. Correlation coefficients for the Geggel and Geggel-real IOL powers compared with ideal IOL power were 0.948 and 0.951, respectively.

The Geggel method was also calculated using the double K method in the following manner. By using the estimated diopters of treatment and the known axial length, the Koch table was used to determine the necessary diopters to be added to the SRK/T formula, which used the pre-IOL keratometry and axial length.[27] This gave the following values: mean±SD 0.07±0.51, absolute mean±SD 0.40±0.33, minimum/maximum −0.92/1.46; 6 eyes between −0.50 and −1.00 D, 8 eyes between −0.50 D and plano, 15 eyes between plano and 0.50 D, 5 eyes between 0.50 and 1.0 D, 2 eyes greater than 1.0 D, and 81% within −1.0/+0.5 D. These results are slightly worse than the derived linear regression formula because more hyperopic results occurred.

The Masket and Koch formulas had a low mean hyperopic refractive error and many patients with >0.5 D hyperopia. The Ladas and Walter formulas had low mean values, but higher SDs, wider ranges of results, and smaller percentages with final results within −1.0/+0.5 D. The modified Maloney method worked best using the Hoffer equation. The Holladay and Hoffer equations worked well with the clinical history method, with the Hoffer equation having a lower myopic mean value, lower minimum values, and fewer hyperopic surprises but still no more than 60% within an acceptable refractive range. The Feiz nomogram created less myopia than the standardized Feiz approach. The Latkany flat equation gave more desirable clinical results than the average formula technique with 85% eyes within −1.0/+0.5 D.

For equations using only axial length input, the Ferrara method tended to produce too much myopia, whereas the Rosa technique had less myopia but a low percentage (47%) within the clinically useful range of −1.0/+0.5 D. The Savini and Shammas no-history methods gave outstanding overall results with a low overall mean myopia, minimum amounts of hyperopic error, and 81% to 89% within the acceptable refractive range. The Seitz and Awwad methods worked best with the Hoffer equation; Awwad's method had a trend for more hyperopia. Several methods met published IOL prediction standards and had >55% within ±0.5 D and >85% within ±1 D (Geggel, Geggel-real, Masket, Koch, Latkany average and flat, Savini, Shammas no-history, Seitz Holladay and Hoffer, Awwad Hoffer).[44, 45] However, the best overall results with fewer over corrections were found with the Geggel-real, Shammas no-history equation, Savini, Latkany flat, and Seitz (Hoffer formula) methods. Averaging these 5 values for the 26 eyes that had all the necessary preoperative data produced a consensus score that was similar to the Geggel-real values. Only 4 eyes had hyperopic refractions (0.11, 0.12, 0.24, 0.42), and 96% were within the −1.00/+0.5 D range.

TABLE 3

Comparison of Refractive Results (Diopters)

| Formula | n | Mean | SD | Min | Max | ABS | ABS SD |
|---|---|---|---|---|---|---|---|
| Geggel | 36 | 0.01 | 0.40 | −0.96 | 0.99 | 0.33 | 0.30 |
| Geggel-real | 36 | −0.34 | 0.40 | −1.42 | 0.49 | 0.41 | 0.30 |
| Masket | 26 | 0.35 | 0.52 | −0.71 | 1.63 | 0.53 | 0.33 |
| Koch | 26 | 0.25 | 0.50 | −0.71 | 1.30 | 0.45 | 0.30 |
| Ladas SRK/T | 25 | −0.33 | 1.19 | −2.86 | 2.58 | 0.92 | 0.77 |
| Ladas Hoffer | 25 | 0.07 | 1.12 | −1.73 | 2.75 | 0.83 | 0.72 |
| Walter | 25 | −0.07 | 1.25 | −2.03 | 3.25 | 0.94 | 0.79 |
| Maloney SRK/T | 36 | 0.34 | 0.86 | −1.19 | 2.44 | 0.71 | 0.59 |
| Maloney Holladay | 36 | 0.10 | 0.92 | −1.47 | 2.52 | 0.71 | 0.59 |
| Maloney Hoffer | 36 | −0.43 | 0.74 | −1.73 | 1.41 | 0.75 | 0.40 |
| CHM SRK/T | 25 | 0.36 | 0.71 | −0.83 | 1.41 | 0.63 | 0.47 |
| CHM Holladay | 25 | 0.12 | 0.74 | −1.14 | 1.10 | 0.66 | 0.34 |
| CHM Hoffer | 25 | −0.55 | 0.73 | −2.11 | 0.84 | 0.72 | 0.55 |
| Feiz 1 | 25 | −0.76 | 0.76 | −2.41 | 0.84 | 0.89 | 0.61 |
| Feiz 2/nomogram | 26 | −0.74 | 0.59 | −2.11 | 0.70 | 0.82 | 0.46 |
| Larkany average | 26 | 0.27 | 0.48 | −0.75 | 1.26 | 0.46 | 0.30 |
| Larkany flat | 26 | −0.45 | 0.57 | −1.95 | 0.70 | 0.56 | 0.46 |
| Ferrara | 36 | −1.46 | 0.92 | −3.17 | 0.40 | 1.52 | 0.81 |
| Rosa | 36 | −0.75 | 0.78 | −1.97 | 1.07 | 0.97 | 0.49 |
| Savini | 27 | −0.26 | 0.50 | −1.28 | 0.84 | 0.44 | 0.35 |
| Jin | 36 | −0.37 | 0.88 | −1.89 | 1.71 | 0.76 | 0.57 |
| Shammas no formula | 36 | −0.19 | 0.58 | −1.18 | 1.54 | 0.48 | 0.36 |
| Shammas/rgr SRK/T | 36 | 0.64 | 0.84 | −0.91 | 2.68 | 0.79 | 0.68 |
| Shammas/rgr Holladay | 36 | 0.42 | 0.91 | −1.12 | 2.76 | 0.76 | 0.65 |
| Shammas/rgr Hoffer | 36 | −0.06 | 0.74 | −1.42 | 1.46 | 0.59 | 0.43 |
| Seitz SRK/T | 27 | 0.46 | 0.50 | −0.43 | 1.46 | 0.56 | 0.37 |
| Seitz Holladay | 27 | 0.23 | 0.54 | −0.64 | 1.46 | 0.46 | 0.36 |
| Seitz Hoffer | 27 | −0.35 | 0.44 | −1.26 | 0.56 | 0.44 | 0.34 |
| Awwad SRK/T | 36 | 0.73 | 0.82 | −0.57 | 2.60 | 0.87 | 0.67 |
| Awwad Holladay | 36 | 0.53 | 0.88 | −0.92 | 2.68 | 0.77 | 0.67 |
| Awwad Hoffer | 36 | 0.06 | 0.64 | −1.02 | 1.48 | 0.50 | 0.38 |
| Consensus* | 26 | −0.34 | 0.39 | −1.20 | 0.42 | 0.41 | 0.31 |

ABS = absolute mean; CHM = clinical history method; Consensus* = combining Geggel-real, Shammas no formula, Savini, Latkany flat, and Seitz Hoffer; max = maximum; min = minimum; n = number; rgr = regression; SD = standard deviation.

Discussion of the Study Results

Previous research has identified 2 distinct subsets of formulas and techniques that attempt to predict better IOL powers in patients with previous corneal excimer laser refractive surgery. The first group requires some pre-refractive surgical data.[9,13,14,18,22-24,27,37,41-43] The second group tries to select the proper IOL using only data available before the actual cataract surgery.[15,16,19,25,26,29,31,35,36,39,46-48] These latter methods are clinically more useful because many patients now and in the future will not have their change in SE, pre-laser keratometry, or excimer laser data readily available. Most techniques not requiring preoperative data rely, in some way, on regression formulas derived from empirical data. Many formulas determine an additional diopter power that needs to be added to various lens formulas.[9,14,18,24-27] Numerous studies have confirmed the direct relationship between the change in SE and the required adjustment in IOL formulas.[8-11,13,14,18,24,27,41,46,49-55] The current technique estimates the excimer laser-induced SE change using a new corneal ratio based on simple pachymetric measurements from an instrument available in most surgical practices. This number is then used in a regression formula to determine the dioptric power to be added to the SRK/T formula to minimize the risk for postoperative hyperopia.

Four steps in the proposed new technique help to minimize hyperopic surprises. First, the estimated ablation depth is divided by 12 and not higher values to maximize the estimated change in SE. Half of the eyes in this study had confirmed VISX version 1.51 or 3.xx ablation profiles that remove approximately 12 μm per diopter of treatment (Table 2). Second, the starting point for the Geggel ratio calculation is 1 SD above its mean. Third, the final calculated value must be at least >10 μm. FIG. 5 confirms that the estimated ablation depth will be above the line representing the actual amount with only a few data points closely below this level. FIG. 6 shows that the estimated treatment values were highly correlated with the actual values. Fourth, the Geggel-real calculation aims for mild myopia as suggested by other authors.[2,10,15,16,26,27,31,32,55-57] Table 4 shows that no eyes had a final refraction more than +0.5 D using these empirical adjustments. Many studies have shown that the double K method reduces hyperopic surprises by minimizing the effective lens position assumptions built into modern-day formulas.[15, 17,29,40,54] Although double K techniques could be used with the Geggel method using Koch's tables, results were not superior to simply using the derived regression formula. This will need to be corroborated by future studies with a new set of patients.

TABLE 4

| Comparison of Final Refractive Ranges (Diopters) | | | | | | | | | |
|---|---|---|---|---|---|---|---|---|---|
| Formula | n | <−1.50 | −1.0/−1.50 | −1.0/−0.50 | −0.5/plano | 0.0/0.5 | 0.5/1.0 | >1.0 | −1.0/+0.5 (%) |
| Geggel | 36 | | | **3** | **16** | **13** | 4 | | 89 |
| Geggel-real | 36 | | 3 | **7** | **22** | **4** | | | 92 |
| Masket | 26 | | | **1** | **6** | **8** | 10 | 1 | 58 |
| Koch | 26 | | | **2** | **6** | **9** | 8 | 1 | 65 |
| Ladas SRK/T | 25 | 2 | 6 | **4** | **5** | **2** | 4 | 2 | 44 |
| Ladas Hoffer | 25 | 1 | 3 | **5** | **4** | **5** | 4 | 3 | 56 |
| Walter | 25 | 2 | 6 | **1** | **5** | **5** | 4 | 2 | 44 |
| Maloney SRK/T | 36 | | **1** | **5** | 8 | **7** | 7 | 8 | 56 |
| Maloney Holladay | 36 | | 2 | **9** | **7** | 8 | 4 | 6 | 67 |
| Maloney Hoffer | 36 | 2 | 4 | **16** | **5** | **4** | 2 | 3 | 69 |
| CHM SRK/T | 25 | | | **4** | **6** | **4** | 6 | 5 | 56 |
| CHM Holladay | 25 | | 2 | **2** | **8** | **2** | 10 | 1 | 48 |
| CHM Hoffer | 25 | **3** | 5 | **3** | **10** | **2** | 2 | | 60 |
| Feiz 1 | 25 | 3 | 9 | **3** | **5** | **4** | 1 | | 48 |
| Feiz 2/nomogram | 26 | t | 7 | **11** | **4** | **2** | 1 | | 65 |
| Larkany average | 26 | | | **1** | **7** | **9** | 8 | **1** | 65 |
| Larkany flat | 26 | 1 | 2 | **8** | **11** | **3** | 1 | | 85 |
| Ferrara | 36 | 15 | 13 | **3** | **2** | **3** | | | 22 |
| Rosa | 36 | 6 | 9 | **12** | 3 | 2 | 3 | 1 | 47 |
| Savini | 27 | | **2** | **6** | **10** | 8 | 1 | | 89 |
| Jin | 36 | 3 | 7 | 6 | 8 | 8 | 2 | 2 | 61 |
| Shammas no formula | 36 | | **2** | 8 | **19** | **2** | 3 | 2 | 81 |
| Shammas/rgr SRK/T | 36 | | | 1 | 11 | 5 | 8 | 11 | 44 |
| Shammas/rgr Holladay | 36 | | 1 | 4 | 8 | 9 | 5 | 9 | 58 |
| Shammas/rgr Hoffer | 36 | | 2 | 8 | **14** | **4** | 4 | 4 | 72 |
| Seitz SRK/T | 27 | | | | **7** | **6** | **12** | 2 | 48 |
| Seitz Holladay | 27 | | | **3** | 8 | **8** | 6 | 2 | 70 |
| Seitz Hoffer | 27 | | 2 | **7** | **12** | **5** | **1** | | 89 |
| Awwad SRK/T | 36 | | | 2 | **5** | **8** | 9 | 12 | 42 |
| Awwad Holladay | 36 | | | **4** | **7** | **8** | 7 | 10 | 53 |
| Awwad Hoffer | 36 | | | 7 | 10 | 11 | 5 | 3 | 78 |
| Consensus* | 26 | | 1 | **6** | **15** | **4** | | | 96 |

ABS = absolute mean; CHM = clinical history method; Consensus* = combining Geggel-real, Shammas no formula, Savini, Latkany flat, and Seitz Hoffer. Bolded numbers reprint acceptable postoperative refractive range; max = maximum; min = minimum; n = number; rgr = regression; SD = standard deviation.

The different formulas that use the change in SE to derive a diopter value to be added to the SRK/T IOL calculation produce results differing by as much as 1.2 D for a 5.0 D preoperative manifest refraction (4.40 D corrected to corneal plane for Masket and revised [Hill] Masket): Masket 1.53 D [(−0.326X laser SE+0.101)]; revised (Hill) Masket 1.96 D [(−0.4385X laser SE+0.0295)]; Feiz nomogram 2.74 D [(0.595X|ΔSE|−0.231)], Geggel 1.6 D[(−0.399X ΔSE −0.40)], Latkany average 2.09 [−(0.46SE+0.21)], and Latkany flat 1.5 D [−(0.475E+0.85)].[9,14,18,21,24,41] All formulas input keratometry values differently. Latkany uses the average or flat keratometry values calculated using the clinical history method or topography to derive the initial SRK/T value so the flatter keratometry value will result in a higher initial IOL number and the modification a lower value to compensate. The initial Masket formula used IOL-Master keratometry values. Feiz used a manual keratometer to derive the formula and the IOLMaster values to test its efficacy in a later study. Inasmuch as each keratometer and topographer may give differing keratometry values because of the number and location of corneal measurements, further studies using different instruments will be necessary to verify the new formula in this study. All comparative IOL numbers in the current study used identical manual Haag-Streit keratometry values except where otherwise noted, such as the modified Maloney and Shammas regression formula where topography values were used according to the original studies.

The Geggel formula could be simplified mathematically to 0.40 (|ΔSE|−1), with ΔSE representing the estimated excimer laser treatment (D) at the corneal plane. Its final value approximates other values even though the change in SE is reduced by 1 D because the Geggel ratio starts at the 1 SD above the mean. In addition, as noted by other investigators, the formula reveals that if estimated laser treatment is off by 1 D, the additional IOL power will have a 0.4 D error, which translates to only 0.27 D in refractive error.[14, 58]

Few studies have compared differing third-generation formulas for overall effectiveness in this group of patients.[8, 15,16,29,32,40,54,59] Although Hoffer himself states that his formula works best in short eyes with axial lengths <22 mm, and most LASIK/PRK eyes are much longer (average axial length in this study 25.81±1.37 mm), most studies have shown that the Hoffer Q formula works best in these LASIK eyes.[8,15,16,32,60] This occurs because the Hoffer Q formula has the lowest IOL adjustment for the double K method as measured by Koch.[27] The Hoffer Q formula squares the tangent of the keratometry value to determine the effective lens position. This mathematic manipulation of keratometry values reduces this effective lens position error close to the Haigis L formula, which uses anterior chamber depth and not keratometry to determine the effective lens position.[16] Tables 3 and 4 show that the Hoffer equation works best for the Ladas, modified Maloney, clinical history method, Shammas regression, and Awwad equations compared with the SRK/T and Holladay 1 formulas.

Randleman et al[20] recently proposed the consensus-K technique because of the great variability of any given method, Many previous methods have used the clinical history method as the gold standard.[4,8,10,16,32,33,38,40,59] However, numerous studies have shown that this is not ideal for several reasons: difficulty in obtaining the necessary data, results skewed by development of nuclear sclerosis, probable false assumption of 1:1 ratio of change in SE and keratometry value, and poor results when applied to patients post-LASIK.[2,4,8,9,15,18,21,24,31,32,41,50,58,61,62] The current study uses the ideal IOL power as the gold standard. A new consensus group consisting of those methods that yielded the best overall results (Geggel-real, Shammas no-history equation, Savini, Latkany flat, and Seitz [Hoffer formula] methods) had impressive results (Tables 3 and 4). The first 2 methods require no pre-refractive surgical data.[29] The latter 3 require change in SE but use the data in different ways. The Savini method alters the refractive index and uses the double K method.[37] The Latkany method adds an additional power to the calculated SRK/T formula.[1821] The Seitz method lowers the keratometry value used in the Hoffer formula in the present study.[13] This new consensus method deserves future study in a larger cohort.

There are several advantages and limitations to the current retrospective study. All patients received the identical IOL with a personalized A constant and were evaluated by the inventor with the same topographer and keratometer. Most, but not all, patients had axial length measurements with the IOL Master, which helps to eliminate some of the inherent errors in IOL studies.[26] Most eyes (78%) had surgery performed by one surgeon. All eyes had postoperative measurements taken at least 4 weeks (average close to 3 months) after uneventful and successful surgery. The superior corneal spot was chosen as a reference point for the Geggel ratio for several reasons. This area is not involved in flap creation during LASIK using a superior hinge micro-keratome compared with possible nasal and temporal flap decentrations. In addition, it is not treated with the laser during either LASIK or PRK and is protected by the upper lid during normal postoperative healing. It is more consistently easier to measure with the pachymeter probe than the peripheral inferior, temporal, and nasal corneal areas. One previous study used a peripheral/central corneal thickness index to distinguish between keratoconus and contact lens-induced corneal thinning.[63] The mean value of 4 readings (superior, nasal, inferior, temporal) at the 5 to 7-mm zone measured with the Orbscan was used. This measurement would not work with the current proposed technique because most excimer laser treatments remove tissue within the central 8-mm zone. In the future, other machines such as the pentacam may be programmed to measure directly this 2-mm peripheral corneal region. The surgeon must measure the thinnest central pachymetry in a standard way, and care must be taken in placing the probe perpendicular to the superior corneal area. The surgeon, rather than numerous technicians, should perform both measurements. The majority of eyes in this study had laser treatment with the VISX machine. One patient in this study had confirmed bilateral surgery with the Nidek excimer laser. Different laser machines and ablation profiles (standard, blended, and wavefront) remove differing amounts of tissue per diopter of treatment. Further studies are needed to verify the reliability of the proposed regression formula in these patients. The formula was generated from eyes receiving myopic or mixed astigmatism excimer ablations and would not be expected to work for hyperopic treatments that do not affect central corneal pachymetry. Table 1 reveals an overlap in the Geggel ratio ranges between the 3 arbitrary divisions based on superior corneal pachymetry. This helps to explain the need to use lower or higher values if the estimated ablation is >105 μm or <10 μm, respectively, for an individual patient.

There may be concern that pachymetry changes over time. With confocal studies, Patel et al[64] demonstrated that stromal and corneal thickness is unchanged from 1 month to 7 years post-LASIK and from 1 to 7 years post-PRK. The average time from laser to cataract surgery in this study was 8 years. If corneal thickness ratios remain relatively stable beyond this time, then the formula in this study should still be reliable. The pachymetric method assumes that the total amount of tissue removed during either the original or secondary enhancement surgeries is no more than 105 μm. There will be an underestimation of SE change in those with greater ablation depths. As previous authors have noted, any article reporting a new formula or method tends to show superior results with its own data set.[65, 66]

As noted above, the aforementioned Geggel ratio and associated mathematical calculations, assumptions and rules may be embodied in software, may reside on a computer-readable medium, may be implemented via a network, may be incorporated in one or more medical devices, or any combination thereof. For example, some embodiments may include a device or system including a processor operatively coupled to a tangible computer-readable medium. The computer-readable medium may have stored thereon instructions which, if executed by the processor, cause the processor to implement one or more of the calculations, assumptions and rules described herein. Those skilled in the art will readily recognize various systems in which the teachings of the present disclosure may be realized.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

REFERENCES

1. Lesher M, Schumer J, Hunkeler J, et al. Phacoemulsification with intraocular lens implantation after excimer photorefrac-tive keratectomy: a case report. J Cataract Refract Surg 1994; 20(suppl): 265-7.
2. Gimbel H V, Sun R, Furlong M T, et al. Accuracy and predictability of intraocular lens power calculation after photorefrac-tive keratectomy. J Cataract Refract Surg 2000; 26:1147-51.
3. Randleman J B, Loupe D N, Song C D, et al. Intraocular lens power calculations after laser in situ keratomileusis. Cornea 2002; 21:751-5.
4. Kalski R S, Danjoux J P, Fraenkel G E, et al. Intraocular lens power calculation for cataract surgery after photorefractive keratectomy for high myopia. J Refract Surg 1997; 13:362-6.
5. Gimbel H V, Sun R. Accuracy and predictability of intraocular lens power calculation after laser in situ keratomileusis. J Cataract Refract Surg 2001; 27:571-6.
6. Morris A H, Whittaker K W, Morris R J, Corbett M C. Errors in intraocular lens power calculation after photorefractive keratectomy [letter]. Eye 1998; 12:327-8.
7. Ladas J G, Boxer Wachter B S, Hunkeler J D, Durrie D S. Intraocular lens power calculations using corneal topography after photorefractive keratectomy. Am J Ophthalmol 2001; 132:254-5.
8. Odenthal M T, Eggink C A, Melles G, et al. Clinical and theoretical results of intraocular lens power calculation for cataract surgery after photorefractive keratectomy for myopia, Arch Ophthalmol 2002; 120:431-8.
9. Feiz V, Mannis M J, Garcia-Ferrer F, et al. Intraocular lens power calculation after laser in situ keratomileusis for myopia and hyperopia: a standardized approach. Cornea 2001; 20: 792-7.
10. Hamed A M, Wang L, Misra M, Koch D D. A comparative analysis of five methods of determining corneal refractive power in eyes that have undergone myopic laser in situ keratomileusis. Ophthalmology 2002; 109:651-8.
11. Kim J H, Lee D H, Joo C K. Measuring corneal power for intraocular lens power calculation after refractive surgery: comparison of methods. J Cataract Refract Surg 2002; 28: 1932-8.
12. Langenbucher A, Haigis W, Seitz B. Difficult lens power calculations. Curr Opin Ophthalmol 2004; 15:1-9.
13. Seitz B, Langenbucher A, Nguyen N X, et al. Underestimation of intraocular lens power for cataract surgery after myopic photorefractive keratectomy. Ophthalmology 1999; 106:693-702.
14. Masket S, Masket S E. Simple regression formula for intraocular lens power adjustment in eyes requiring cataract surgery after excimer laser photoablation. J Cataract Refract Surg 2006; 32:430-4.
15. Wang L, Booth M A, Koch D D. Comparison of intraocular lens power calculation methods in eyes that have undergone LASIK. Ophthalmology 2004; 111:1825-31.
16. Haigis W. Intraocular lens calculation after refractive surgery for myopia: Haigis-L formula. J Cataract Refract Surg 2008; 34:1658-63.
17. Aramberri J. Intraocular lens power calculation after corneal refractive surgery: double-K method. J Cataract Refract Surg 2003; 29:2063-8.
18. Latkany R A, Chokshi A R, Speaker M G, et al. Intraocular lens calculations after refractive surgery. J Cataract Refract Surg 2005; 31:562-70.
19. Mackool R J, Ko W, Mackool R. Intraocular lens power calculation after laser in situ keratomileusis: aphakic refraction technique. J Cataract Refract Surg 2006; 32:435-7.
20. Randleman J B, Foster J B, Loupe D N, et al. Intraocular lens power calculations after refractive surgery: consensus-K technique. J Cataract Refract Surg 2007; 33:1892-8.
21. Khalil M, Chokshi A, Latkany R, et al. Prospective evaluation of intraocular lens calculation after myopic refractive surgery, J Refract Surg 2008; 24:33-8.
22. Ladas J G, Stark W J. Calculating IOL power after refractive surgery [letter]. J Cataract Refract Surg 2004; 30:2458.
23. Walter K A, Gagnon M R, Hoopes P C Jr, Dickinson P J. Accurate intraocular lens power calculation after myopic laser in situ keratomileusis, bypassing corneal power. J Cataract Refract Surg 2006; 32:425-9.
24. Feiz V, Moshirfar M, Mannis M J, et al. Nomogram-based intraocular lens power adjustment after myopic photorefrac-tive keratectomy and LASIK: a new approach. Ophthalmology 2005; 112:1381-7.
25. Ferrara G, Cennamo G, Marotta G, Loffredo E. New formula to calculate corneal power after refractive surgery. J Refract Surg 2004; 20:465-71.
26. Qazi M A, Cua I Y, Roberts C J, Pepose J S. Determining corneal power using Orbscan II videokeratography for intraocular lens calculation after excimer laser surgery for myopia. J Cataract Refract Surg 2007; 33:21-30.
27. Koch D D, Wang L. Calculating IOL power in eyes that have had refractive surgery. J Cataract Refract Surg 2003; 29: 2039-42.
28. Camellin M, Calossi A. A new formula for intraocular lens power calculation after refractive corneal surgery. J Refract Surg 2006; 22:187-99.
29. Shammas H J, Shammas M C. No-history method of intraocular lens power calculation for cataract surgery after myopic laser in situ keratomileusis. J Cataract Refract Surg 2007; 33: 31-6.
30. Ianchulev T, Salz J, Hoffer K, et al. Intraoperative optical refractive biometry for intraocular lens power estimation without axial length and keratometry measurements. J Cataract Refract Surg 2005; 31:1530-6.
31. Jin G J, Crandall A S, Jin Y. Analysis of intraocular lens power calculation for eyes with previous myopic LASIK. J Refract Surg 2006; 22:387-95.
32. Argento C, Cosentino M J, Badoza D. Intraocular lens power calculation after refractive surgery. J Cataract Refract Surg 2003; 29:1346-51.
33. Shammas H J, Shammas M C, Garabet A, et al. Correcting the corneal power measurements for intraocular lens power calculations after myopic laser in situ keratomileusis. Am J Ophthalmol 2003; 136:426-32.

34. Rosa N, Capasso L, Romano A. A new method of calculating intraocular lens power after photorefractive keratectomy. J Refract Surg 2002; 18:720-4.

35. Rosa N, Capasso L, Lanza M, et al. Reliability of a new correcting factor in calculating intraocular lens power after refractive corneal surgery. J Cataract Refract Surg 2005; 31: 1020-4.

36. Borasio E, Stevens J, Smith G T. Estimation of true corneal power after keratorefractive surgery in eyes requiring cataract surgery: BESSt formula. J Cataract Refract Surg 2006; 32: 2004-14.

37. Savini G, Barboni P, Zanini M. Correlation between attempted correction and keratometric refractive index of the cornea after myopic excimer laser surgery. J Refract Surg 2007; 23:461-6.

38. Jarade E F, Tabbara K F. New formula for calculating intraocular lens power after laser in situ keratomileusis. J Cataract Refract Surg 2004; 30:1711-5.

39. Gelender H. Orbscan II-assisted intraocular lens power calculation for cataract surgery following myopic laser in situ keratomileusis (an American Ophthalmological Society thesis). Trans Am Ophthalmol Soc 2006; 104:402-13.

40. Fam H B, Lim K L. A comparative analysis of intraocular lens power calculation methods after myopic excimer laser surgery. J Refract Surg 2008; 24:355-60.

41. Awwad S T, Manasseh C, Bowman R W, et al. Intraocular lens power calculation after myopic laser in situ keratomileusis: estimating the corneal refractive power. J Cataract Refract Surg 2008; 34:1070-6.

42. Holladay J T. Consultations in refractive surgery: IOL calculations following radial keratotomy surgery [comment]. Refract Corneal Surgery 1989; 5:203.

43. Guyton D. Consultations in refractive surgery [comment]. Refract Corneal Surg 1989; 5:203.

44. Holladay J. Standardizing constants for ultrasonic biometry, keratometry, and intraocular lens power calculations. J Cataract Refract Surg 1997; 23:1356-70.

45. Gale R P, Saldana M, Johnston R L, et al. Benchmark standards for refractive outcomes after NHS cataract surgery. Eye 2009; 23:149-52. Epub 2007 Aug. 24.

46. Sonego-Krone S, Lopez-Moreno G, Beaujon-Balbi O V, et al. A direct method to measure the power of the central cornea after myopic laser in situ keratomileusis. Arch Ophthalmol 2004; 122:159-66.

47. Srivannaboon S, Reinstein D Z, Sutton H F, Holland S P. Accuracy of Orbscan total optical power maps in detecting refractive change after myopic laser in situ keratomileusis. J Cataract Refract Surg 1999; 25:1596-9.

48. Zeh W G, Koch D D. Comparison of contact lens overrefraction and standard keratometry for measuring corneal curvature in eyes with lenticular opacity. J Cataract Refract Surg 1999; 25:898-903.

49. Langenbucher A, Torres F, Behrens A, et al. Consideration of the posterior corneal curvature for assessment of corneal power after myopic LASIK. Acta Ophthalmol Scand 2004; 82: 264-9.

50. Stakheev A A, Balashevich L J. Corneal power determination after previous corneal refractive surgery for intraocular lens calculation. Cornea 2003; 22:214-20.

51. Schafer S, Kurzinger G, Spraul C W, Kampmeier J. Comparative results of keratometry with three different keratometers after LASIK [in German]. Klin Monatsbl Augenheilkd 2005; 222:419-23.

52. Maeda N, Klyce S D, Smolek M K, McDonald M B. Disparity between keratometry-style readings and corneal power within the pupil after refractive surgery for myopia. Cornea 1997; 16: 517-24.

53. Rosa N, Cennamo G, Rinaldi M. Correlation between refractive and corneal topographic changes after photorefractive keratectomy for myopia. J Refract Surg 2001; 17: 129-33.

54. Savini G, Barboni P, Zanini M. Intraocular lens power calculation after myopic refractive surgery: theoretical comparison of different methods. Ophthalmology 2006; 113:1271-82.

55. Seitz B, Langenbucher A. Intraocular lens power calculation in eyes after corneal refractive surgery. J Refract Surg 2000; 16:349-61.

56. Probst L E, Holladay J T. Corneal refractive power after myopic LASIK [letter]. Ophthalmology 2003; 110:1857.

57, Hoffer K J. Calculating intraocular lens power after refractive corneal surgery. Arch Ophthalmol 2002; 120: 500-1.

58. Koch D D. New options for IOL calculations after refractive surgery. J Cataract Refract Surg 2006; 32:371-2.

59. Cheng A C, Rao S S, Lau S, et al. Comparison of techniques for corneal power assessment after myopic LASIK without the use of preoperative data. J Refract Surg 2008; 24:539-43.

60. Hoffer K J. The Hoffer Q formula: a comparison of theoretic and regression formulas. J Cataract Refract Surg 1993; 19: 700-12.

61. Speicher L. Intra-ocular lens calculation status after corneal refractive surgery. Curr Opin Ophthalmol 2001; 12:17-29.

62. Seitz B, Langenbucher A, Haigis W. Pitfalls of IOL power prediction after photorefractive keratectomy for high myopia—case report, practical recommendations and literature review [in German]. Klin Monatsbl Augenheilkd 2002; 219: 840-50.

63. Pflugfelder S C, Liu Z, Feuer W, Verm A. Corneal thickness indices discriminate between keratoconus and contact lens-induced corneal thinning. Ophthalmology 2002; 109: 2336-41.

64. Patel S V, Erie J C, McLaren J W, Bourne W M. Confocal microscopy changes in epithelial and stromal thickness up to 7 years after LASIK and photorefractive keratectomy for myopia. J Refract Surg 2007; 23:385-92.

65. Holladay J T, Prager T C, Ruiz R S, et al. Improving the predictability of intraocular lens power calculations. Arch Oph-thalmol 1986; 104:539-41.

66. Retzlaff J A, Sanders D R, Kraff M C. Development of the SRK/T intraocular lens implant power calculation formula. J Cataract Refract Surg 1990; 16:333-40.

What is claimed is:

1. A method for determining an intraocular lens (IOL) power for a patient having a refractively modified cornea, the method comprising:

receiving an initial IOL power value determined using the SRK/T formula;

receiving a central pachymetry (CP) measurement and a superior corneal pachymetry (SCP) measurement for a cornea of the patient;

determining an estimated laser ablation depth by equating a first value to a second value, wherein the first value is a ratio of the sum of the CP measurement and the estimated laser ablation depth to the SCP measurement, and wherein the second value is related to a mean value of a sample of ratios of CP measurements to SCP measurements for a plurality of corneas that have not been refractively modified;

determining an IOL power adjustment value using the estimated laser ablation depth; and adding the IOL power adjustment value to the initial IOL power to obtain a corrected IOL power value.

2. The method of claim 1, further comprising:

performing a superior corneal pachymetry measurement and a central keratometry measurement on the cornea; and calculating the initial IOL power using the superior corneal pachymetry and central keratometry measurements.

3. The method of claim 1, wherein the second value is one standard deviation above the mean value of the sample of ratios of CP measurements to SCP measurements for a plurality of corneas that have not been refractively modified.

4. The method of claim 1, wherein determining an IOL power adjustment value using the estimated laser ablation depth comprises:

determining an estimated laser treatment amount by dividing the estimated laser ablation depth by a value related to known actual laser ablation depths per laser treatment amounts.

5. The method of claim 4, wherein the value related to known actual laser ablation depths per laser treatment amounts is equal to 12 micrometers per diopter (D).

6. The method of claim 4, wherein determining an IOL power adjustment value using the estimated laser ablation depth further comprises:

inputting the estimated laser treatment amount into a derived regression equation.

7. The method of claim 1, wherein the second value is one standard deviation above the mean value of the sample of ratios of CP measurements to SCP measurements for a plurality of corneas that have not been refractively modified, and wherein determining an estimated laser ablation depth further comprises:

comparing the estimated laser ablation depth to a minimum laser ablation depth;

if the estimated laser ablation depth is less than the minimum laser ablation depth, adding one standard deviation of the sample of ratios to the second value to obtain a third value; and equating the first value to the third value.

8. The method of claim 1, wherein the second value is one standard deviation above the mean value of the sample of ratios of CP measurements to SCP measurements for a plurality of corneas that have not been refractively modified, and wherein determining an estimated laser ablation depth further comprises:

comparing the estimated laser ablation depth to a maximum laser ablation depth;

if the estimated laser ablation depth is greater than the maximum laser ablation depth, subtracting one standard deviation of the sample of ratios from the second value to obtain a third value; and equating the first value to the third value.

9. The method of claim 1, further comprising:

determining a selectable IOL power value using the corrected IOL power value according to the following rules, wherein X represents an integer number of diopters:

for corrected IOL power values of (X−1)+0.4 diopters to (X−1)+0.7 diopters, choose X diopters for the selectable IOL power value; and for corrected IOL power values of (X−1)+0.8 diopters to (X)+0.3 diopters, choose (X+0.5) diopters for the selectable IOL power value.

10. A medical device configured to determine an intraocular lens (IOL) power for patients having a refractively modified cornea, the medical device comprising:

a computing device; and a tangible computer-readable medium having instructions stored thereon that, if executed by the computing device, cause the computing device to perform operations comprising:

receiving an initial IOL power value determined using a formula;

receiving a central pachymetry (CP) measurement and a superior corneal pachymetry (SCP) measurement for a cornea of a patient;

determining an estimated laser ablation depth by equating a first value to a second value, wherein the first value is a ratio of the sum of the CP measurement and the estimated laser ablation depth to the SCP measurement, and wherein the second value is related to a mean value of a sample of ratios of CP measurements to SCP measurements for a plurality of corneas that have not been refractively modified;

determining an IOL power adjustment value using the estimated laser ablation depth; and adding the IOL power adjustment value to the initial IOL power to obtain a corrected IOL power value.

11. The medical device of claim 10, wherein the formula is selected from the group consisting of the Hoffer formula, the SRK/T formula, the Holladay formula, and the Haigis formula.

12. The medical device of claim 10, further comprising:

a measurement device operative to perform a superior corneal pachymetry measurement and a central keratometry measurement on a cornea of a patient.

13. The medical device of claim 10, wherein the operations further comprise:

determining an estimated laser treatment amount by dividing the estimated laser ablation depth by a value related to known actual laser ablation depths per laser treatment amounts.

14. The medical device of claim 10, wherein the second value is one standard deviation above the mean value of the sample of ratios of CP measurements to SCP measurements for a plurality of corneas that have not been refractively modified, and wherein the operations further comprise:

comparing the estimated laser ablation depth to a minimum laser ablation depth;

if the estimated laser ablation depth is less than the minimum laser ablation depth, adding one standard deviation of the sample of ratios to the second value to obtain a third value; and equating the first value to the third value.

15. The medical device of claim 10, wherein the second value is one standard deviation above the mean value of the sample of ratios of CP measurements to SCP measurements for a plurality of corneas that have not been refractively modified, and wherein the operations further comprise:

comparing the estimated laser ablation depth to a maximum laser ablation depth;

if the estimated laser ablation depth is greater than the maximum laser ablation depth, subtracting one standard deviation of the sample of ratios from the second value to obtain a third value; and equating the first value to the third value.

16. A tangible computer-readable medium having instructions stored thereon that, if executed by a computing device, cause the computing device to perform operations comprising:

receiving an initial IOL power value determined using a formula;

receiving a central pachymetry (CP) measurement and a superior corneal pachymetry (SCP) measurement for a cornea of a patient;

determining an estimated laser ablation depth by equating a first value to a second value, wherein the first value is a ratio of the sum of the CP measurement and the estimated laser ablation depth to the SCP measurement, and wherein the second value is related to a mean value of a sample of ratios of CP measurements to SCP measurements for a plurality of corneas that have not been refractively modified;

determining an IOL power adjustment value using the estimated laser ablation depth; and adding the IOL power adjustment value to the initial IOL power to obtain a corrected IOL power value.

17. The tangible computer-readable medium of claim 16, wherein the formula is selected from the group consisting of the Hoffer formula, the SRK/T formula, the Holladay formula, and the Haigis formula.

18. The tangible computer-readable medium of claim 16, wherein the operations further comprise:

determining an estimated laser treatment amount by dividing the estimated laser ablation depth by a value related to known actual laser ablation depths per laser treatment amounts.

19. The tangible computer-readable medium of claim 16, wherein the operations further comprise:

calculating the initial IOL power using the SCP and CP measurements.

20. The tangible computer-readable medium of claim 16, wherein the second value is one standard deviation above the mean value of the sample of ratios of CP measurements to SCP measurements for a plurality of corneas that have not been refractively modified, and wherein the operations further comprise:

comparing the estimated laser ablation depth to a minimum laser ablation depth;

if the estimated laser ablation depth is less than the minimum laser ablation depth, adding one standard deviation of the sample of ratios to the second value;

comparing the estimated laser ablation depth to a maximum laser ablation depth; and if the estimated laser ablation depth is greater than the maximum laser ablation depth, subtracting one standard deviation of the sample of ratios from the second value.

* * * * *